United States Patent [19]
Lord et al.

[11] Patent Number: 5,390,671
[45] Date of Patent: Feb. 21, 1995

[54] TRANSCUTANEOUS SENSOR INSERTION SET

[75] Inventors: Peter C. Lord, Santa Clarita; William P. Van Antwerp, Brentwood; John J. Mastrototaro, Los Angeles; Paul S. Cheney, II, Beverly Hills; Nannette M. Schnabel, Valencia, all of Calif.

[73] Assignee: MiniMed Inc., Sylmar, Calif.

[21] Appl. No.: 213,101

[22] Filed: Mar. 15, 1994

[51] Int. Cl.6 ............... A61B 5/05; A61B 5/04
[52] U.S. Cl. ................... 128/635; 128/637; 128/634; 128/642; 204/403; 606/129
[58] Field of Search ............. 128/635, 637, DIG. 6, 128/632, 634, 642; 606/108, 129; 604/51, 52; 204/403

[56] References Cited

U.S. PATENT DOCUMENTS

| | | |
|---|---|---|
| 3,399,674 | 9/1968 | Pannier et al. . |
| 3,878,830 | 4/1975 | Bicher ................. 178/635 |
| 4,141,365 | 2/1979 | Fischell et al. ......... 128/642 |
| 4,562,751 | 1/1986 | Nason et al. . |
| 4,573,994 | 3/1986 | Fischell et al. . |
| 4,678,408 | 7/1987 | Nason et al. . |
| 4,685,903 | 8/1987 | Cable et al. . |
| 4,953,552 | 9/1990 | DeMarzo ................. 204/403 |
| 5,071,408 | 12/1991 | Ahmed .................. 606/108 |
| 5,108,819 | 4/1992 | Heller et al. . |
| 5,299,571 | 4/1994 | Mastrototaro ............ 128/637 |

Primary Examiner—Lee S. Cohen
Assistant Examiner—Bria M. Greer
Attorney, Agent, or Firm—Kelly Bauersfeld & Lowry

[57] ABSTRACT

An insertion set is provided for transcutaneous placement of a sensor such as a glucose sensor at a selected site within the body of a patient. The insertion set comprises a slotted insertion needle extending through a mounting base adapted for mounting onto the patient's skin. A flexible thin film sensor includes a proximal segment carried by the mounting base and defining conductive contacts adapted for electrical connection to a suitable monitor, and a distal segment protruding from the mounting base with sensor electrodes for transcutaneous placement. The proximal and distal segments of the sensor are linearly offset or misaligned, with the distal segment fitted within the insertion needle for transcutaneous sensor placement with the needle as the mounting base is pressed onto the patient's skin. The insertion needle can then be withdrawn to leave the sensor distal segment at the selected insertion position with the sensor electrodes in contact with patient blood or other extracellular fluid.

23 Claims, 3 Drawing Sheets

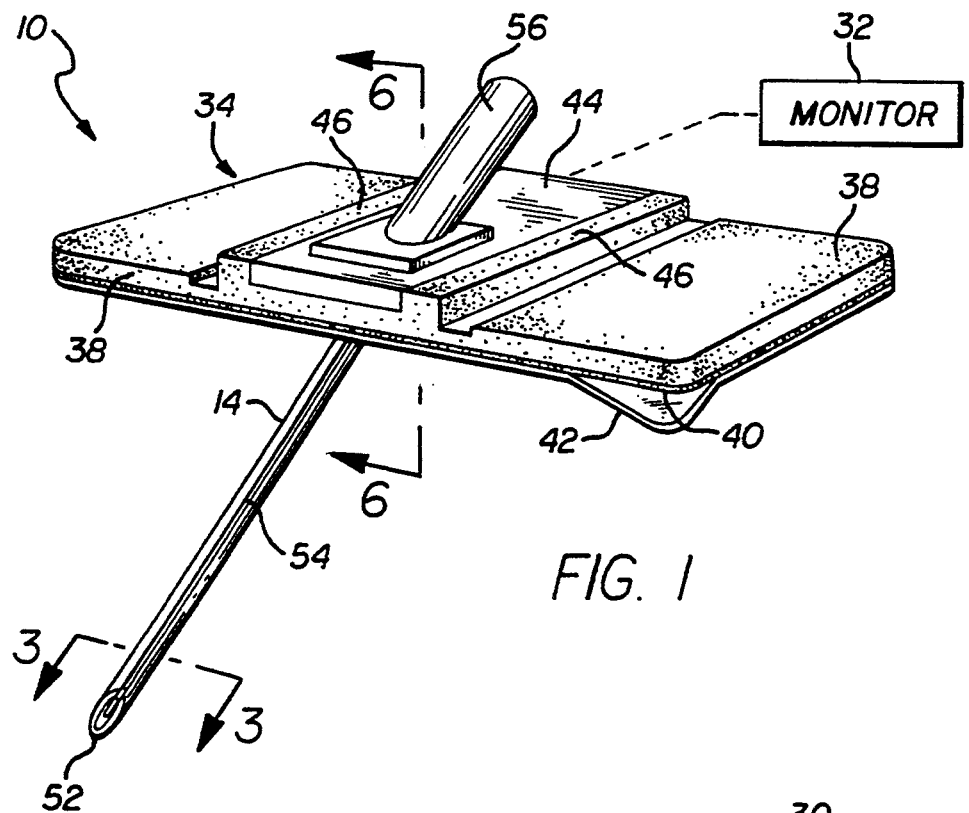
FIG. 1
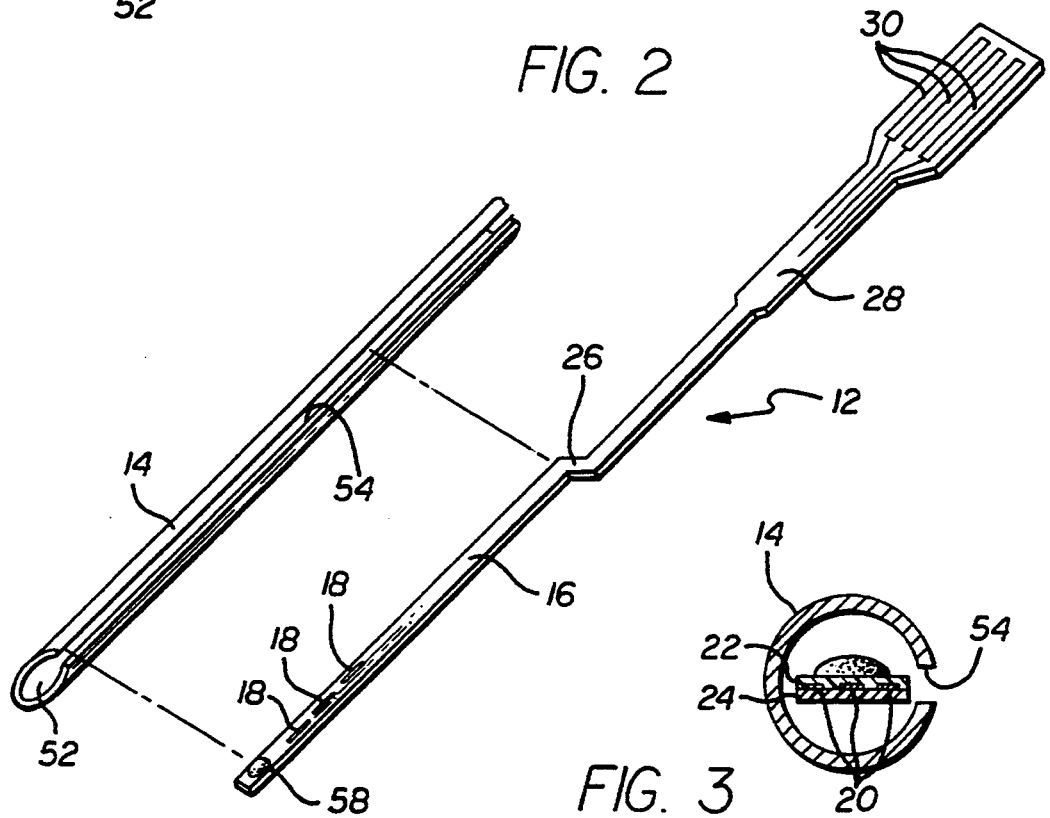
FIG. 2
FIG. 3

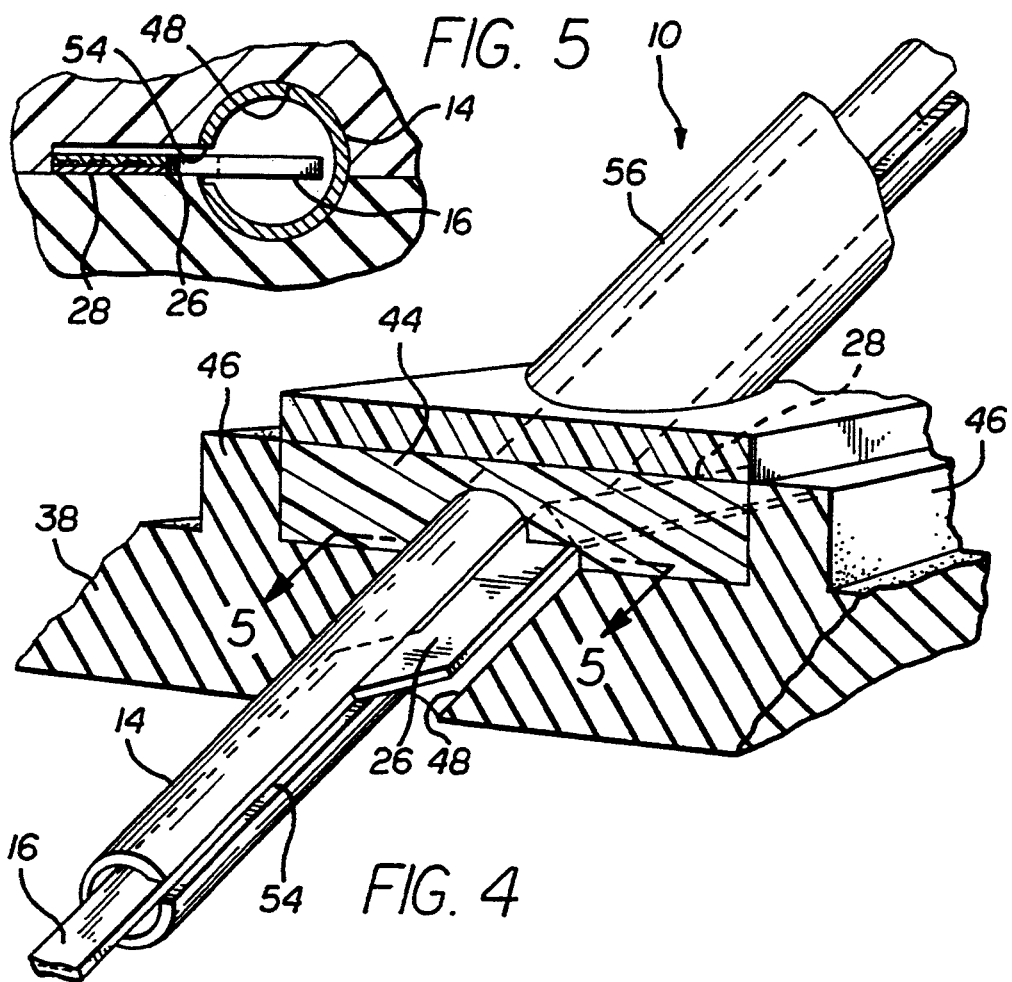
FIG. 5
FIG. 4
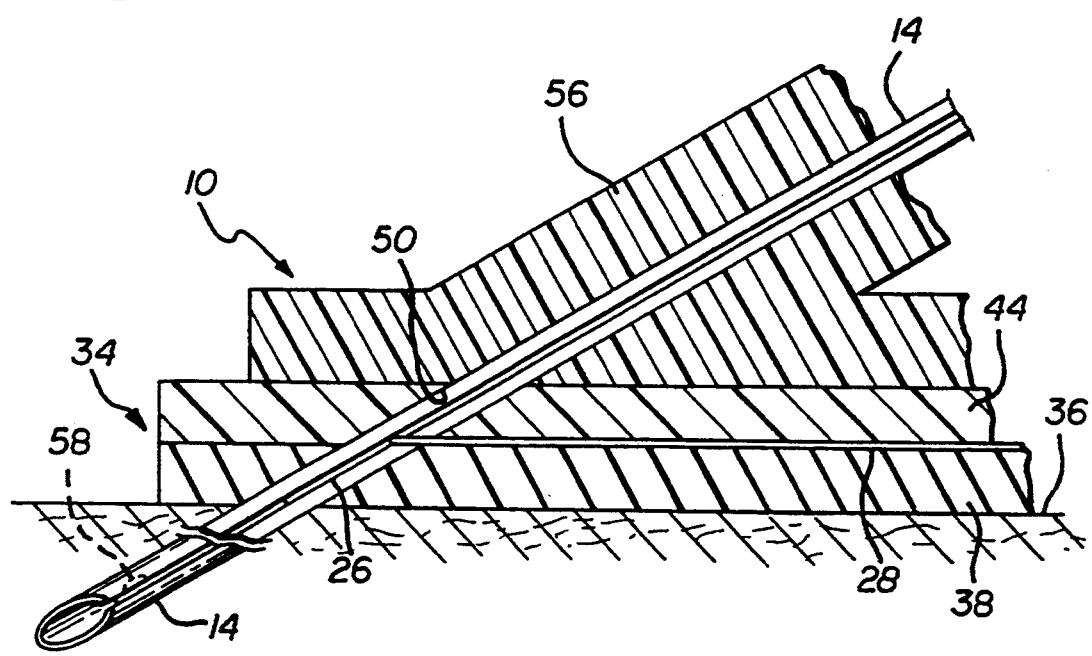
FIG. 6

TRANSCUTANEOUS SENSOR INSERTION SET

BACKGROUND OF THE INVENTION

This invention relates generally to devices and methods for placing a sensor at a selected site within the body of a patient. More specifically, this invention relates to an improved and relatively simple insertion set for quick and easy transcutaneous placement of a flexible thin film sensor of the type used, for example, to obtain periodic blood glucose readings.

In recent years, a variety of electrochemical sensors have been developed for a range of applications, including medical applications for detecting and/or quantifying specific agents in a patient's blood. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semiautomated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for transcutaneous placement in direct contact with patient blood or the like, and exposed conductive contacts at an externally located proximal end for convenient electrical connection with a suitable monitor device. Such thin film sensors hold significant promise in patient monitoring applications, but unfortunately have been difficult to place transcutaneously with the sensor electrodes in direct contact with patient blood or other extracellular fluid.

The present invention relates specifically to a sensor insertion set and related thin film sensor adapted for quickly and easily placing the sensor on a patient with sensor electrodes in direct contact with patient blood or other extracellular fluid.

SUMMARY OF THE INVENTION

In accordance with the invention, a subcutaneous insertion set is provided for placing a flexible sensor such as a thin film electrochemical sensor at a selected site within the body of a patient. The insertion set comprises a slotted insertion needle extending through a mounting base adapted for seated mounting onto the patient's skin. A flexible thin film sensor includes a proximal segment carried by the mounting base, and a distal segment protruding from the mounting base and having sensor electrodes thereon. The proximal and distal segments of the sensor are linearly offset or misaligned so that the distal segment can be fitted into the slotted insertion needle for transcutaneous placement as the mounting base is pressed onto the patient's skin. The insertion needle can be withdrawn from the mounting base, leaving the sensor distal segment at the selected position within the patient, such as a subcutaneous, intravascular, intramuscular, or intravenous site. Conductive contacts on the sensor proximal end can be electrically connected to a suitable monitor device so that appropriate blood chemistry readings can be taken.

In the preferred form, the sensor proximal and distal segments are formed generally in parallel offset relation, with a short transition segment extending angularly therebetween. The proximal segment is mounted on the mounting base in a position disposed generally parallel to the patient's skin, when the mounting base is seated upon the patient's skin. The transition segment of the sensor is angularly folded for reception of the sensor distal segment to a position generally coaxially within the slotted insertion needle. A retention member such as a bead of cured epoxy may be carried on the sensor distal segment to prevent lateral separation of the sensor from the insertion needle.

The distal segment of the flexible sensor is transcutaneously placed as the insertion needle pierces the patient's skin upon press-on placement of the mounting base onto the patient's skin. The insertion needle can then be withdrawn from the patient and the mounting base. During such withdrawal, the insertion needle slides over the sensor distal segment, thereby leaving the sensor distal segment at the selected site.

In one alternative preferred form of the invention, the retention member may comprise a length of tubing secured to the sensor distal segment and extending therefrom to an external position outside the patient. This tubing defines a small bore lumen which may be used subsequently to introduce medication to the patient or otherwise to introduce a selected sensor calibration fluid in the vicinity of the sensor electrodes for periodic sensor calibration functions.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating a transcutaneous sensor insertion set embodying the novel features of the invention;

FIG. 2 is an enlarged fragmented exploded perspective view illustrating assembly of portions of the transcutaneous sensor insertion set of FIG. 1;

FIG. 3 is an enlarged fragmented sectional view taken generally on the line 3—3 of FIG. 1;

FIG. 4 is an enlarged fragmented perspective view showing slide-fit assembly of an insertion needle and flexible sensor of the sensor insertion set;

FIG. 5 is an enlarged fragmented sectional view taken generally on the line 5—5 of FIG. 4;

FIG. 6 is an enlarged fragmented sectional view taken generally on the line 6—6 of FIG. 1;

DETAILED DESCRIPTION OF THE PREFERRED EMBODIMENTS

Figure 7:
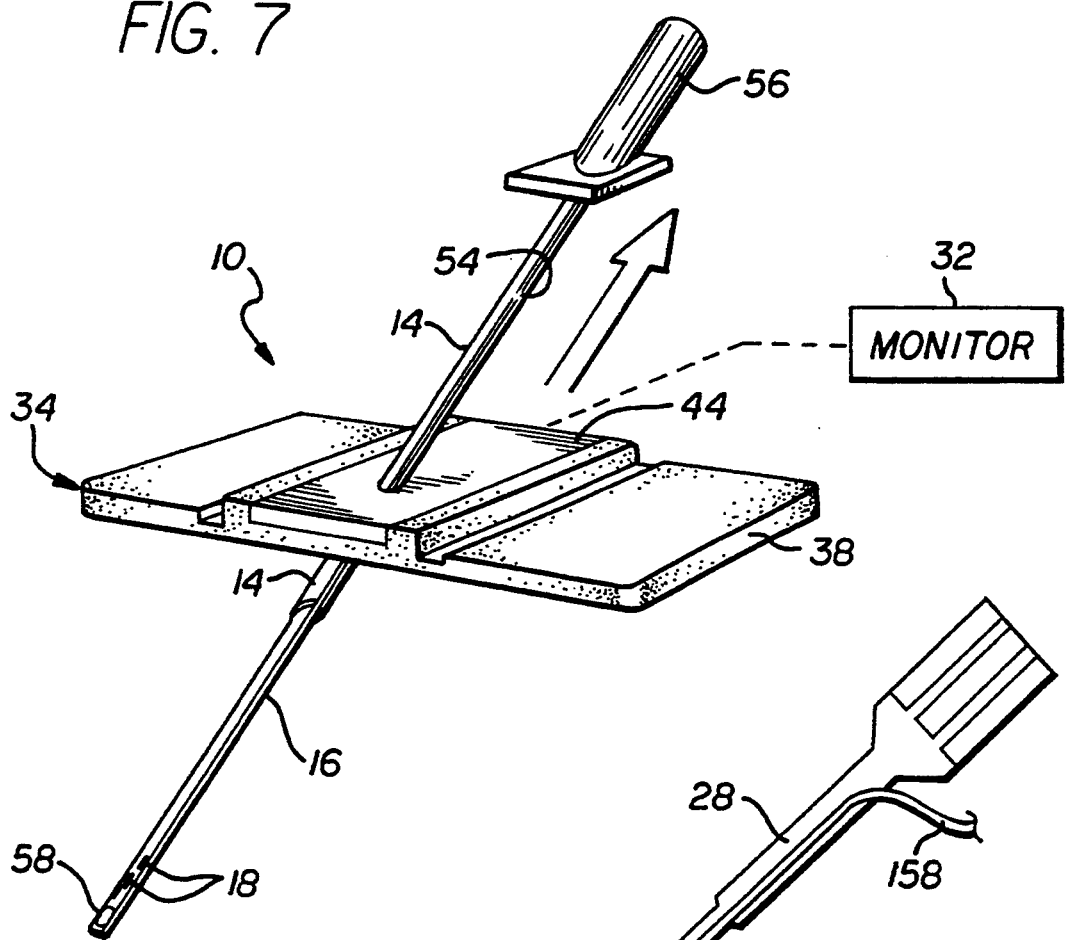
FIG. 7 is a perspective view illustrating withdrawal of the insertion needle from the flexible sensor.

As shown in the exemplary drawings, an improved sensor insertion set referred to generally in FIG. 1 by the reference numeral 10 is provided for transcutaneous placement of a flexible sensor 12 (FIG. 2) at a selected site within the body of a patient. The insertion set 10 includes a rigid hollow insertion needle 14 for quick and easy transcutaneous placement of a sensor distal segment 16 having one or more exposed sensor electrodes 18 thereon. The insertion needle 14 is then withdrawable to leave the sensor electrodes 18 in place at the selected site.

The transcutaneous sensor insertion set 10 of the present invention is particularly designed for facilitating accurate placement of a flexible thin film electrochemical sensor of the type used for monitoring specific blood parameters representative of patient condition. The insertion set 10 is designed to place the sensor subcutaneously or at another selected site within the body of a patient, in a manner minimizing patient discomfort and trauma. In one preferred application, the sensor 12 may be designed to monitor blood glucose levels, and may be used in conjunction with automated or semiautomated medication infusion pumps of the external or implantable type as described in U.S. Pat. Nos. 4,562,751; 4,678,408; 4,685,903 or 4,573,994, to deliver insulin to a diabetic patient.

As shown best in FIGS. 2 and 3, the flexible electrochemical sensor 12 is constructed according to so-called thin film mask techniques to include elongated thin film conductors 20 embedded or encased between upper and lower layers 22 and 24 of a selected insulative material such as polyimide film or sheet. The sensor electrodes 18 at a tip end of the distal segment 16 are exposed through the upper layer 22 for direct contact with patient blood, when the sensor is transcutaneously placed. The distal segment 16 is joined by an angularly extending or offset transition segment 26 to a proximal segment 28, the end of which terminates in conductive contact pads 30 which are also exposed through the upper insulative layer 22. As is known in the art, and illustrated schematically in FIG. 1, these contact pads 30 are adapted for electrical connection to a suitable monitor 32 for monitoring patient condition in response to signals derived from the sensor electrodes 18. Further description of flexible thin film sensors of this general type may be formed in copending U.S. Serial No. (MiniMed Docket MT-0222), filed concurrently herewith, (Docket 34279), entitled METHOD OF FABRICATING THIN FILM SENSORS, which is incorporated by reference herein.

The sensor 12 is carried by a mounting base 34 adapted for placement onto the skin 36 (FIG. 6) of a patient. As shown, the mounting base 34 comprises an enlarged and generally rectangular flexible foam pad 38 having an underside surface coated with a suitable pressure sensitive adhesive 40 (FIG. 1). A peel-off paper strip 42 is normally provided to cover and protect the adhesive layer 40, until the insertion set 10 is ready for use.

As shown in FIGS. 4 and 5, the proximal segment 28 of the flexible sensor 12 is sandwiched between the flexible pad 38 and an overlying support plate 44 which may be conveniently positioned between upstanding rails 46 formed on the flexible pad. The proximal sensor segment 28 has a forwardmost end joined to the transition segment 26 folded angularly downwardly within a keyhole slot 48 formed in the flexible pad 38. That is, as shown in FIG. 5, the keyhole slot 48 includes a narrow and relatively straight slit protruding radially from one side of a circular aperture. The transition segment 26 of the flexible sensor 12 folds angularly downwardly into the slit and then extends laterally into the circular aperture whereat the transition segment 26 is joined with the distal sensor segment 16. The keyhole slot 48 is shown to extend angularly through the pad 38 at an angle of about forty-five degrees, although it will be understood that other angular orientations up to ninety degrees may be used.

The insertion needle 14 is adapted for slide-fit reception through a circular needle port 50 formed in the support plate 44, and further through the circular aperture of the keyhole slot 48 in the flexible mounting pad 38. As shown in FIGS. 1 and 2, the insertion needle 14 has a sharpened tip 52 and an open narrow slot 54 which extends longitudinally from the tip 52 along one side of the needle to a position at or near a hub 56 at the rear end thereof. The insertion needle 14 fits through the support plate 44 and keyhole slot 48 of the mounting base 34, with the needle slot 54 laterally facing the straight slit portion of the keyhole slot 48. With this arrangement, as shown in FIGS. 4 and 6, the transition segment 26 between the sensor distal and proximal segments 16 and 28 projects laterally through the needle slot 54 so that the sensor distal segment is coaxially aligned within the insertion needle 14, but linearly misaligned or offset with respect to the sensor proximal segment 28.

In use, the insertion set 10 permits quick and easy transcutaneous placement of the sensor distal segment 16 at a selected site within the body of the patient. More specifically, the peel-off strip 42 (FIG. 1) is removed from the pad 38, at which time the mounting base 34 can be pressed onto and seated upon the patient's skin. During this step, the insertion needle 14 pierces the patient's skin 36 (FIG. 6) and carries the sensor distal segment 16 therein to the appropriate transcutaneous placement site. A retention member 58 such as a cured bead of epoxy or the like may be placed on the sensor distal segment 16, at one or more positions along the length thereof, to prevent inadvertent lateral separation of the sensor distal segment from the insertion needle. In this regard, the retention member 58 in combination with the thickness of the sensor 12, provides a dimension greater than the width of the needle slot 54, thereby preventing sideways separation of the sensor through the needle slot (FIG. 3).

When the sensor is transcutaneously placed, with the mounting base 34 seated upon the patient's skin, the insertion needle 14 can be withdrawn from the patient. During this withdrawal step, as illustrated in FIG. 7, the insertion needle 14 slides over the sensor distal segment 16, leaving the sensor electrodes 18 at the selected insertion site. The conductive contact pads 30 on the sensor proximal segment 28 are appropriately coupled to the monitor 32, so that the sensor 12 can then be used over a prolonged period of time for taking blood chemistry readings, such as blood glucose readings in a diabetic patient.

Figure 8:
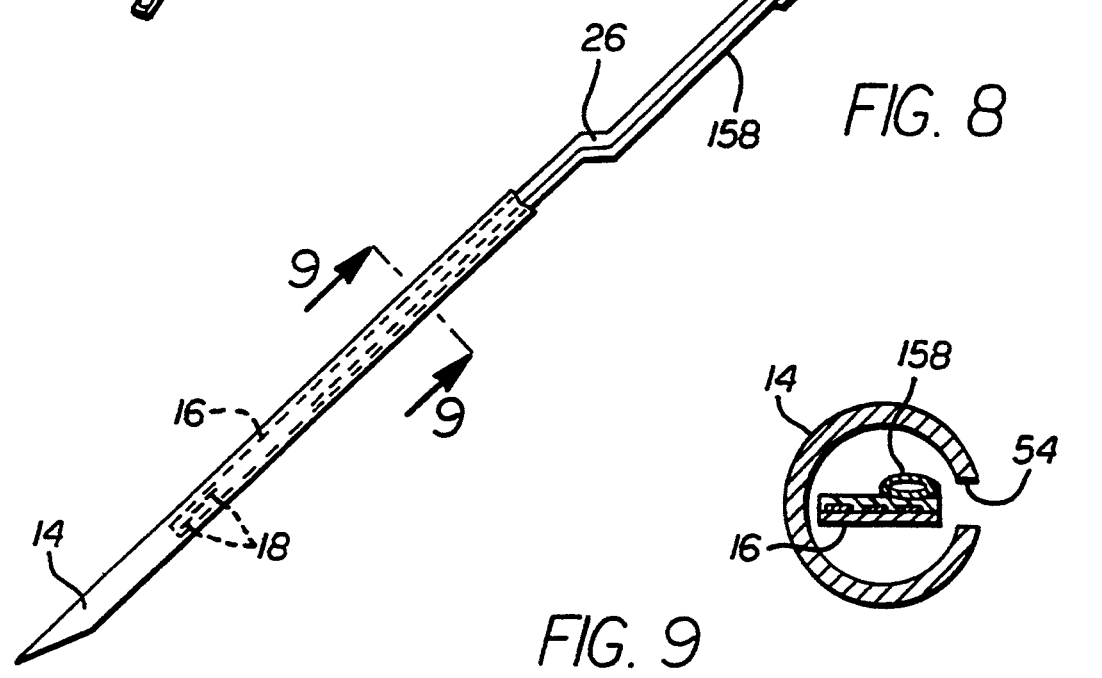
FIG. 8 is a plan view illustrating an assembled insertion needle and sensor embodying an alternative preferred form of the invention.
Figure 9:
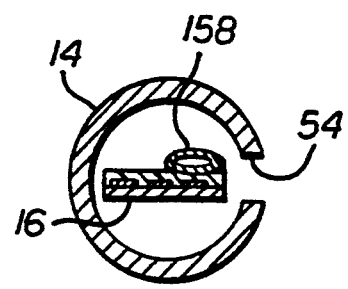
FIG. 9 is an enlarged sectional view taken generally on the line 9—9 of FIG. 8.

FIGS. 8 and 9 show one alternative preferred embodiment of the invention, wherein a modified retention member 158 is provided in the form of a length of flexible tubing attached to the sensor 12. This tubing 158 extends through the insertion needle to a point outside the body of the patient, as by following the contour of the flexible sensor along the transition and proximal segments 26 and 28. The tubing 158 provides a convenient transcutaneous lumen for administration of medication to the patient, as desired. Alternatively, the tubing 158 defines a path through which a selected calibration fluid can be administered to the patient, at a location directly proximate to the sensor electrodes 18. In this regard, when the sensor electrodes are designed for obtaining periodic glucose level readings, occasional recalibration of those electrodes may be necessary or desirable to ensure accurate blood glucose readings.

The transcutaneous sensor insertion set of the present invention thus provides a relatively simple device for quickly and easily placing a flexible thin film electrochemical sensor at a selected position within a patient. The slotted insertion needle permits use of a relatively narrow gage needle, thereby minimizing patient trauma and related discomfort.

A variety of modifications and improvements to the transubcutaneous sensor insertion set of the present invention will be apparent to those skilled in the art. Accordingly, no limitation on the invention is intended by way of the foregoing description and accompanying drawings, except as set forth in the appended claims.

What is claimed is:

1. A transcutaneous sensor insertion set, comprising:
   a mounting base adapted for mounting onto a patient's skin;
   a flexible sensor having a proximal segment carried by said mounting base, and a distal segment protruding from said mounting base and having at least one sensor electrode thereon, said proximal and distal segments being misaligned with respect to each other; and
   a hollow insertion needle carried by said mounting base to protrude therefrom and having said distal segment of said sensor received therein, said insertion needle defining a longitudinally extending slot along one side thereof to permit sliding withdrawal of said needle from said mounting base and said distal segment of said sensor.

2. The transcutaneous sensor insertion set of claim 1 wherein said sensor further includes a transition segment interconnecting said proximal and distal segments in laterally offset relation, said transition segment extending through said needle slot when said distal segment is received within said needle.

3. The transcutaneous sensor insertion set of claim 1 further including a retention member on said sensor distal segment to prevent lateral displacement of said sensor distal segment through said needle slot.

4. The transcutaneous sensor insertion set of claim 3 wherein said retention member comprises a bead of cured epoxy.

5. The transcutaneous sensor insertion set of claim 3 wherein said retention member comprises a length of tubing connected to said sensor distal segment and extending therefrom to a position outside the patient when the sensor distal segment is transcutaneously placed.

6. The transcutaneous sensor insertion set of claim 1 wherein said sensor is a flexible thin film sensor.

7. The transcutaneous sensor insertion set of claim 1 wherein said sensor is an electrochemical sensor.

8. The transcutaneous sensor insertion set of claim 1 wherein said sensor is a glucose sensor.

9. The transcutaneous sensor insertion set of claim 1 wherein said insertion needle has a sharp tip and a rear end with a hub mounted thereon to facilitate manual withdrawal of said needle from said mounting base and said sensor distal segment.

10. The transcutaneous sensor insertion set of claim 1 wherein said insertion needle extends through an open port formed in said mounting base, in generally coaxial alignment with said sensor distal segment for slide-fit reception of said sensor distal segment within said needle, said insertion needle being positioned to pierce a patient's skin to carry said sensor distal segment to an insertion position within the patient upon placement of said mounting base onto the patient's skin, said insertion needle being slidably withdrawable from the patient's skin and said mounting base to leave said sensor distal segment at the insertion position.

11. The transcutaneous sensor insertion set of claim 1 wherein said sensor proximal segment includes at least one exposed conductive contact.

12. The transcutaneous sensor insertion set of claim 1 wherein said mounting base includes means for removable attachment thereof to the patient's skin.

13. A transcutaneous sensor insertion set, comprising:
   a mounting base adapted for placement onto a patient's skin;
   a flexible sensor having a proximal segment carried by said mounting base, a distal segment protruding downwardly from said mounting base and having a tip end with at least one sensor electrode thereon, and a transition segment interconnecting said proximal and distal segments in axially misaligned relation; and
   a hollow insertion needle having a longitudinally elongated slot formed along one side thereof, said needle being slidably receivable through an open port formed in said mounting base in generally coaxial alignment with said sensor distal segment for slide-fit reception of said sensor distal segment within said needle, with said sensor transition segment extending through said needle slot;
   said insertion needle being positioned to pierce a patient's skin to carry said sensor distal segment to an insertion position within the patient upon placement of said mounting base onto the patient's skin, said insertion needle being slidably withdrawable from the patient's skin and said mounting base to leave said sensor distal segment at the insertion position.

14. The transcutaneous sensor insertion set of claim 13 wherein said mounting base supports said sensor proximal segment in angular relation to said sensor distal segment.

15. The transcutaneous sensor insertion set of claim 13 further including a retention member on said sensor distal segment to prevent lateral displacement of said sensor distal segment through said needle slot.

16. The transcutaneous sensor insertion set of claim 15 wherein said retention member comprises a bead of cured epoxy.

17. The transcutaneous sensor insertion set of claim 15 wherein said retention member comprises a length of tubing connected to said sensor distal segment and extending therefrom to a position outside the patient when the sensor distal segment is transcutaneously placed, said tubing defining a transcutaneous fluid flow path for selectively delivering fluid to and from a position proximate to said sensor electrode.

18. The transcutaneous sensor insertion set of claim 13 wherein said sensor is a flexible thin film sensor.

19. The transcutaneous sensor insertion set of claim 13 wherein said sensor proximal segment includes at least one exposed conductive contact.

20. A transcutaneous sensor insertion set, comprising:
a flexible sensor having a proximal segment with at least one conductive contact, a distal segment with at least one sensor electrode, a transition segment interconnecting said proximal and distal segments in axially misaligned relation, and at least one conductor extending within said sensor from said conductive contact to said sensor electrode; and
a mounting base adapted for placement onto a patient's skin, said mounting base including means for supporting said sensor proximal segment in a position with said sensor distal segment protruding downwardly from said mounting base.

21. The transcutaneous sensor insertion set of claim 20 wherein said mounting base comprises a pad adapted for placement onto the patient's skin and having said sensor proximal segment carried thereon, said sensor transition segment being folded relative to said sensor proximal segment to extend through a port formed in said pad.

22. The transcutaneous sensor insertion set of claim 21 wherein said port formed in said pad has a generally keyhole shape defining a relatively straight slit extending radially from a generally circular aperture, said sensor transition segment being folded to extend from said proximal segment through said straight slit to said distal segment at a position within said circular aperture.

23. The transcutaneous sensor insertion set of claim 22 further including a hollow insertion needle having a longitudinally extending slot formed in one side thereof, said needle being slidably receivable through said circular aperture for slide-fit reception of said sensor distal segment therein, with said sensor transition segment extending through said needle slot, said insertion needle being positioned to pierce a patient's skin to carry said sensor distal segment to an insertion position within the patient upon placement of said mounting base onto the patient's skin, said insertion needle being slidably withdrawable from the patient's skin and said mounting base to leave said sensor distal segment at the insertion position.

* * * * *